US 11,965,847 B2
Apr. 23, 2024

(12) United States Patent
Ligouras et al.

(54) RECONFIGURABLE ARCHITECTURE ANALOG FRONT END FOR ELECTROCHEMICAL SENSORS

(71) Applicant: NXP B.V., Eindhoven (NL)

(72) Inventors: Costantino Ligouras, Utrecht (NL); Sergio Andrés Rueda Gómez, Eindhoven (NL); Harry Neuteboom, Eindhoven (NL); Muhammad Kamran, Helmond (NL); Dave Sebastiaan Kroekenstoel, Eindhoven (NL); Rinze Ida Mechtildis Peter Meijer, Herkenbosch (NL)

(73) Assignee: NXP B.V., Eindhoven (NL)

( * ) Notice: Subject to any disclaimer, the term of this patent is extended or adjusted under 35 U.S.C. 154(b) by 31 days.

(21) Appl. No.: 17/553,274

(22) Filed: Dec. 16, 2021

(65) Prior Publication Data

US 2023/0194451 A1 Jun. 22, 2023

(51) Int. Cl.
*G01N 27/327* (2006.01)
*G01N 27/02* (2006.01)
*G01N 33/483* (2006.01)

(52) U.S. Cl.
CPC ....... *G01N 27/028* (2013.01); *G01N 33/4836* (2013.01)

(58) Field of Classification Search
CPC .................. G01N 33/4836; G01N 27/028
See application file for complete search history.

(56) References Cited

U.S. PATENT DOCUMENTS

| 11,394,394 B1* | 7/2022 | Nittala | H03F 1/26 |
| 2005/0212534 A1* | 9/2005 | Cottis | G01N 17/02 |
| | | | 324/71.2 |
| 2008/0154101 A1* | 6/2008 | Jain | A61B 5/1459 |
| | | | 600/309 |
| 2009/0178937 A1* | 7/2009 | Taylor | G01N 27/3273 |
| | | | 205/792 |
| 2010/0169035 A1* | 7/2010 | Liang | A61B 5/14865 |
| | | | 702/65 |
| 2014/0083864 A1* | 3/2014 | Rowhani | G01N 27/27 |
| | | | 204/412 |
| 2021/0113131 A1* | 4/2021 | Lee | G01N 33/493 |
| 2022/0061690 A1* | 3/2022 | Tansley | A61B 5/0809 |

OTHER PUBLICATIONS

Li, Haitao et al., "CMOS Amperometric ADC With High Sensitivity, Dynamic Range and Power Efficiency for Air Quality Monitoring", IEEE Transactions on Biomedical Circuits and Systems, vol. 10, No. 4, Aug. 2016, pp. 817-827.

(Continued)

*Primary Examiner* — Alesa Allgood

(57) ABSTRACT

A method and apparatus are described for a reconfigurable architecture analog front end architecture for electrochemical sensors. In one example, an analog front end includes an electrode driver stage coupled to electrodes of an electrochemical sensor, and measurement channels coupled to the electrode driver stage to receive an electrode signal from the electrodes of the electrochemical sensor and to generate measurement results, the measurement channels configured to switch configurations to perform different measurements.

21 Claims, 9 Drawing Sheets

(56) References Cited

OTHER PUBLICATIONS

Chung, Wen-Yaw et al. "An Amperometric Sensor Readout Circuit for Multiple Electrochemical Sensor Cells", 2014 International Symposium on Integrated Circuits (ISIC), (2014), pp. 528-531.
Karmokar, Debabrata Kumar et al.; "Analysis of Inverted-F and Loaded Inverted-F Antennas for 2.4 GHz ISM Band Applications"; Journal of Electrical Engineering, The Instutution of Engineers, Bangladesh; vol. EE 36, No. II (Dec. 2009); 6 pages.
Maxell; "Datasheet; Zinc Silver-Oxide Batteries SR626SW"; (May 2004); 3 pages.
NXP; "AN11276—NTAG Antenna Design Guide" Rev. 1.8; (Oct. 2018); 48 pages.
NXP; "AN11578—Energy Harvesting with the Ntag I2C and Ntag I2C plus"; Rev. 1.0; (Feb. 2016); 7 pages.
NXP; "AN12278—Security Solutions for IoT"; (May 2020); 30 pages.
NXP; "AN12283—LPC55S xx Secure Boot"; (Mar. 2020); 23 pages.
NXP; "AN12324—LPC55S xx Usage of the Physically Unclonable Function PUF and Hash Crypt to AES Coding"; (Sep. 2023); 24 pages.
NXP; "AN12326—Secure General-Purpose Input/Output (GPIO) and Usage"; (Jul. 2023); 14 pages.
NXP; "AN12327—Firmware Update Using Secondary Bootloader"; (Oct. 2020); 15 pages.
Zhao, Xiaojie et al.; "Does BTLE measure up against WiFi? A comparison of Indoor location performance"; European Wireless; (May 2014); 6 pages.

* cited by examiner

RECONFIGURABLE ARCHITECTURE ANALOG FRONT END FOR ELECTROCHEMICAL SENSORS

BACKGROUND

Electrochemical sensors are miniaturized making many more types of sensors possible for environmental, production, process control, and other uses. Remote and personal health care monitoring is a growing market with new and improved devices being produced. Wearable fitness trackers measure heartbeats, distance traveled, steps and other impact events. New sensors are being developed to support glucose monitoring, blood oxygen levels and other vital signs that can be measured directly or inferred from other variables detected by the same or by other sensors. These sensors are coupled to readout circuits to digitize the sensed quantity and then combined in systems with wireless interfaces such as Bluetooth, Wi-Fi, and cellular to provide continuous data reports to the patient and health care professionals for In-Patient and Out-Patient monitoring.

The Internet-of-Things (IoT) offers low cost, low power, low data rate communications with a wide range of devices on external networks. IoT has generated particular excitement in healthcare because of its singular potential to improve the health, safety, and quality of life for people everywhere. The semiconductor content in clinical-grade smart IoT edge healthcare devices provides smart processing, analysis, and reporting of many different vital signs.

Electrochemical sensors are used to measure a variety of different chemicals in gaseous and aqueous environments. Oxygen, carbon monoxide, carbon dioxide and airborne pollutants are measured. Water pollutants and biomarkers are also measured. One use of an electrochemical sensor is as a part of an electrocardiogram (ECG) patch. The patch is provided as a self-contained small flat device that can be attached to the body with an adhesive much like a self-adhesive bandage. The ECG patch uses dry electrodes that are directly applied to or connected to the body skin. A signal is applied across the electrodes and the impedance to the signal is measured. Another use is as part of a continuous glucose monitoring (CGM) patch. Different characteristics of the test subject can be measured across the same sensor electrodes to provide a broader range of information.

SUMMARY

A method and apparatus are described for a reconfigurable architecture analog front end architecture for electrochemical sensors. In one example, an analog front end includes an electrode driver stage coupled to electrodes of an electrochemical sensor, and measurement channels coupled to the electrode driver stage to receive an electrode signal from the electrodes of the electrochemical sensor and to generate measurement results, the measurement channels configured to switch configurations to perform different measurements.

In some embodiments, the measurement channels include an input multiplexer to select an input to the respective measurement channel, the analog front end further comprising a controller to operate the input multiplexers based on a sensing mode of the analog front end. In some embodiments, the electrode driver stage comprises a signal generator to generate multiple signals and wherein the analog front end further comprises a controller to operate the signal generator to generate signals based on a sensing mode of the analog front end.

In some embodiments, a first measurement channel of the measurement channels is configured to switch configurations to perform a current measurement, a voltage measurement, and an impedance measurement. In some embodiments, the electrochemical sensor has a Reference Electrode (RE) configured to keep a constant reference voltage by driving a Counter Electrode (CE), and a Work Electrode (WE) and wherein a first measurement channel of the measurement channels comprises a potentiostat circuit. In some embodiments, the electrode driver stage is coupled to the WE and the RE and configured to set a bias setpoint of the potentiostat circuit at a difference between the WE voltage and the RE voltage.

In some embodiments, the electrode driver stage is configured to apply a direct current (DC) setpoint to the WE buffer to measure the current across the electrodes. In some embodiments, the electrode driver stage is configured to set a bias setpoint of the potentiostat circuit at a difference between the WE voltage and the RE voltage and an alternating current (AC) signal is applied to the WE buffer of the first measurement channel to measure the impedance across the electrodes. In some embodiments, the electrode driver stage comprises an RE buffer to drive the RE and wherein the first measurement channel and a second measurement channel of the measurement channels is coupled to the RE buffer, and wherein the RE buffer is configured as a common virtual ground to the WE buffer.

In some embodiments, the measurement channels comprise an analog-to-digital converter (ADC) to generate a measurement result, the ADCs being in a form of a continuous time Sigma Delta ADC with a current input. In some embodiments, an ADC of the first measurement channel of the measurement channels is coupled in a first configuration to convert a current measurement of the electrochemical sensor.

Some embodiments include a down mixer coupled to the WE buffer and to an alternating current applied at the WE, and an input multiplexer between the down mixer and the WE buffer, the input multiplexer being reconfigurable to down mix a WE output current with the alternating current to generate a current related to the WE output current, the down mixer being coupled to the ADC to convert the current to a digital form.

Some embodiments include a second ADC in the form of a second continuous time Sigma Delta ADC with a current input coupled in a configuration to generate an Electrochemical Impedance Spectroscopy measurement. In some embodiments, the electrode driver stage comprises a reference electrode (RE) buffer to drive a reference electrode of the electrochemical sensor and a work electrode (WE) buffer to drive a work electrode of the electrochemical sensor and wherein the RE buffer and the WE buffer have rail-to-rail inputs.

In another example, a health monitoring system includes a controller, a radio frequency system to send measurement results, an electrochemical sensor having electrodes, an electrode driver stage coupled to the electrodes of the electrochemical sensor, and measurement channels coupled to the electrode driver stage to receive an electrode signal from the electrodes of the electrochemical sensor and to generate the measurement results, wherein the controller is coupled to the measurement channels to switch configurations of the measurement channels to perform different measurements.

In some embodiments, the measurement channels include an input multiplexer to select an input to the respective measurement channel, wherein the controller operates the input multiplexers based on a sensing mode of the analog front end, the sensing modes including a current measurement, a voltage measurement, and an impedance measurement.

In some embodiments, the electrodes of the electrochemical sensor comprise a work electrode and reference electrode, wherein the electrode driver stage comprises a work electrode buffer to drive the work electrode and a reference electrode buffer to drive the reference electrode, and wherein the controller sets a voltage at the work electrode buffer and a voltage to the reference electrode buffer with a voltage difference to configure a first measurement channel of the measurement channels in different sink/source output current modes.

In another example a method includes driving electrodes of an electrochemical sensor in a selected one of multiple sensing modes, receiving electrode signals from the electrodes of the electrochemical sensor at multiple measurement channels, and configuring a first measurement channel to perform a measurement of a received electrode signal based on the selected sensing mode.

In some embodiments, driving electrodes comprises setting bias setpoints to drive the electrodes based on the selected one of the multiple sensing modes. In some embodiments, a first measurement channel includes an input multiplexer to select an input to the first measurement channel, wherein configuring the first measurement channel comprises operating the input multiplexer based on the selected sensing mode.

DETAILED DESCRIPTION

Figure 1:
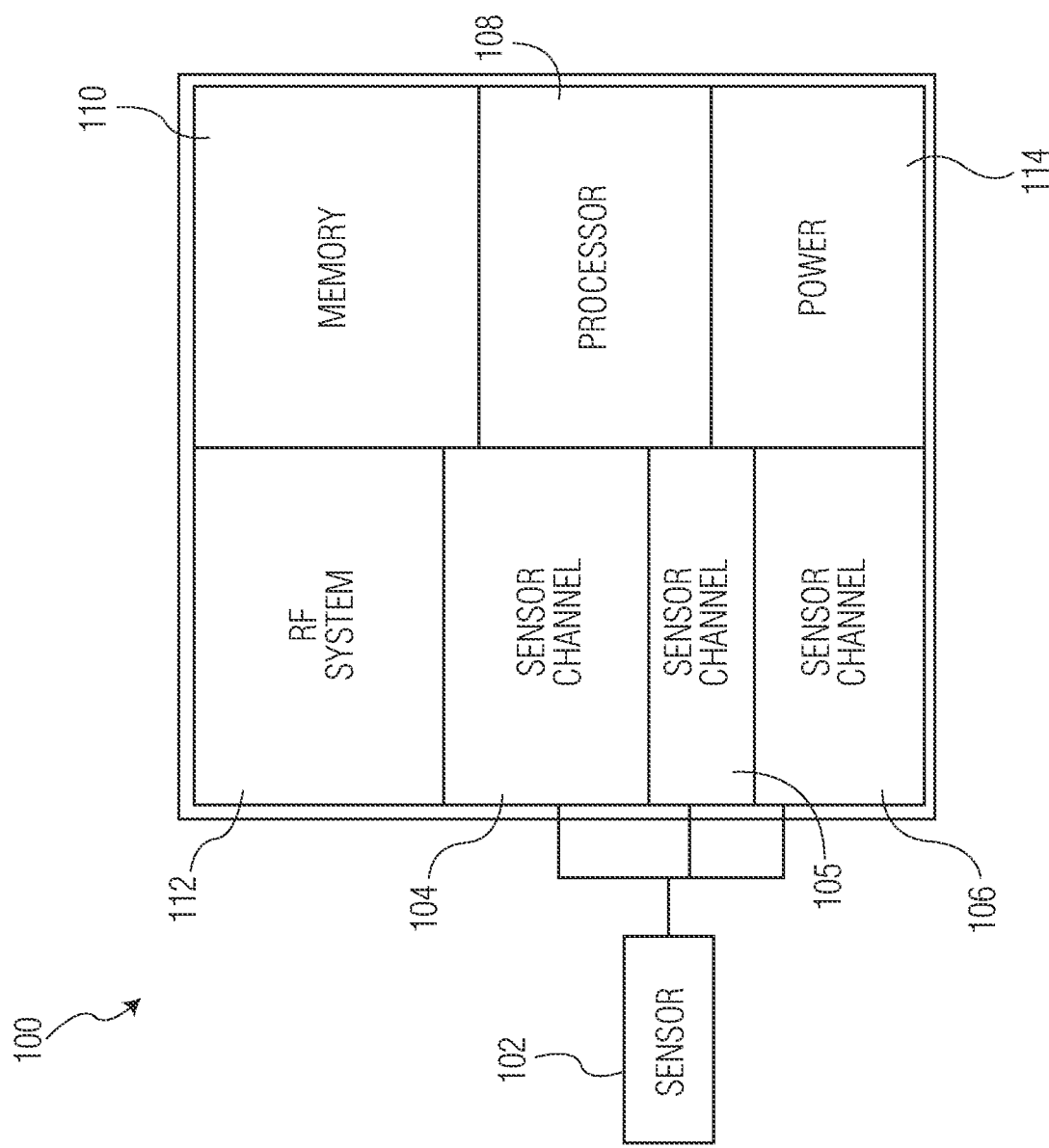
FIG. 1 is a block diagram of a system for measuring parameters of a body.

It will be readily understood that the components of the embodiments as generally described herein and illustrated in the appended drawings could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

A reconfigurable high-precision electrochemical sensor analog front end (AFE) is described herein. The sensor AFE enables amperometric, voltage and impedimetric measurements, for multiple channels simultaneously over a wide range of bias voltages for Continuous Glucose Monitoring and many other applications. In some embodiments, a sensor is built with multiple work electrodes to improve its accuracy. Each work electrode is sensitive to a different biomarker or to the same one with different chemistry. This allows for a combined reading that is more accurate than a single work electrode. For such a sensor, the AFE may have multiple reading channels. The electrochemical measurements may be used for any of a wide variety of different purposes. The measurement device is described as being incorporated into a patch but may also be used with and for other devices and for in-patient and out-patient monitoring. The described implementation may be part of a complete vital signs analog front end (AFE) for an Internet of things (IoT) or other connected device.

An efficient high-precision analog front end architecture for electrochemical sensors is disclosed. The proposed architecture is highly reconfigurable and supports measurements on multiple measurement channels simultaneously. Each measurement can either be a current (or amperometric) measurement, a voltage measurement, or Electrochemical Impedance Spectroscopy (EIS) measurement. The same main building blocks are used for an efficient, cost-effective implementation, as demanded by high volume and even single-use 'disposable' sensory applications FIG. 1 is a block diagram of a health monitoring system such as a smart patch or other system for measuring parameters of a body. The form factor may be modified to suit different purposes and uses. In some embodiments, the power supply is a disposable battery and the processor is a state machine in the form of a Field Programmable Gate Array (FPGA) or microcontroller, microprocessor, or another type of controller to suit a particular application and other functions performed by the system. In some embodiments, the system 100 is 20-40 mm wide and long and less than 5 mm thick with an adhesive strip on one side to attach to the human body in an appropriate place. A strap or band (not shown) may be provided to wrap around an arm or other body part to hold the system 100 in place. The system 100 may have a housing that is moisture and impact resistant with an access port to allow service to batteries and other components.

The health monitoring system 100 has one or more sensors 102 to make electrical contact with the human body. The sensor 102 has electrodes that are coupled to a reconfigurable array of multiple measurement channels, a first measurement channel 106, a second measurement channel 105 and a third measurement channel 106 to be configured to measure current, voltage or impedance across the electrodes when the electrodes are electrically coupled to the body. The measurement channels 104, 105, 106 are coupled to a processor 108 for processing the measured values for controlling an applied signal across the electrodes and for controlling other components of the system.

The processor 108 is further optionally coupled to other sensors (not shown) to measure parameters of the surrounding environment, such as environmental temperature, pressure, and humidity, depending on the particular implementation. The processor 108 may use and communicate other sensor data in any suitable way. The processor is coupled to a memory 110 to store data from the measurement channels and other values determined by the processor or received from other components.

The processor and memory are further coupled to a radio frequency (RF) system 112 that provides communication to external components that may include network nodes, a user interface, and further sensors. In some embodiments, the RF system uses near-field communications. In some embodiments, the RF system is passive or operates as an energy harvester by being energized by an external RF source to modulate the external received RF energy. In some embodiments, the system 100 communicates with a smart phone (not shown) through an RF interface to provide information to the user and may also send information to a health monitoring facility. In another use example, the system communicates with a cellular or Wi-Fi network node to send information directly to a health care facility. The health care facility may then provide alerts to the user through any desired means. The RF system 112 may use one or more wireless communications systems and protocols including NFC, RFID, Bluetooth, Wi-Fi and cellular. Each of the components are also coupled directly or indirectly to a power supply 114 which may be in the form of a battery, a solar cell, a kinetic energy harvester, a thermal energy harvester or any other suitable power source or combination of sources.

The system 100 may be in the form of a single integrated circuit (IC) or some of the components may be combined while other components are not. The multiple components may be combined into a single package for example as a multi-chip module (MCM) or system in a package (SiP) or other physical implementation. Additional components may be added to the system 100 and fewer components may be used. Some functions may be provided on different modules than as described herein. More or fewer modules may be provided than as shown herein.

Figure 2:
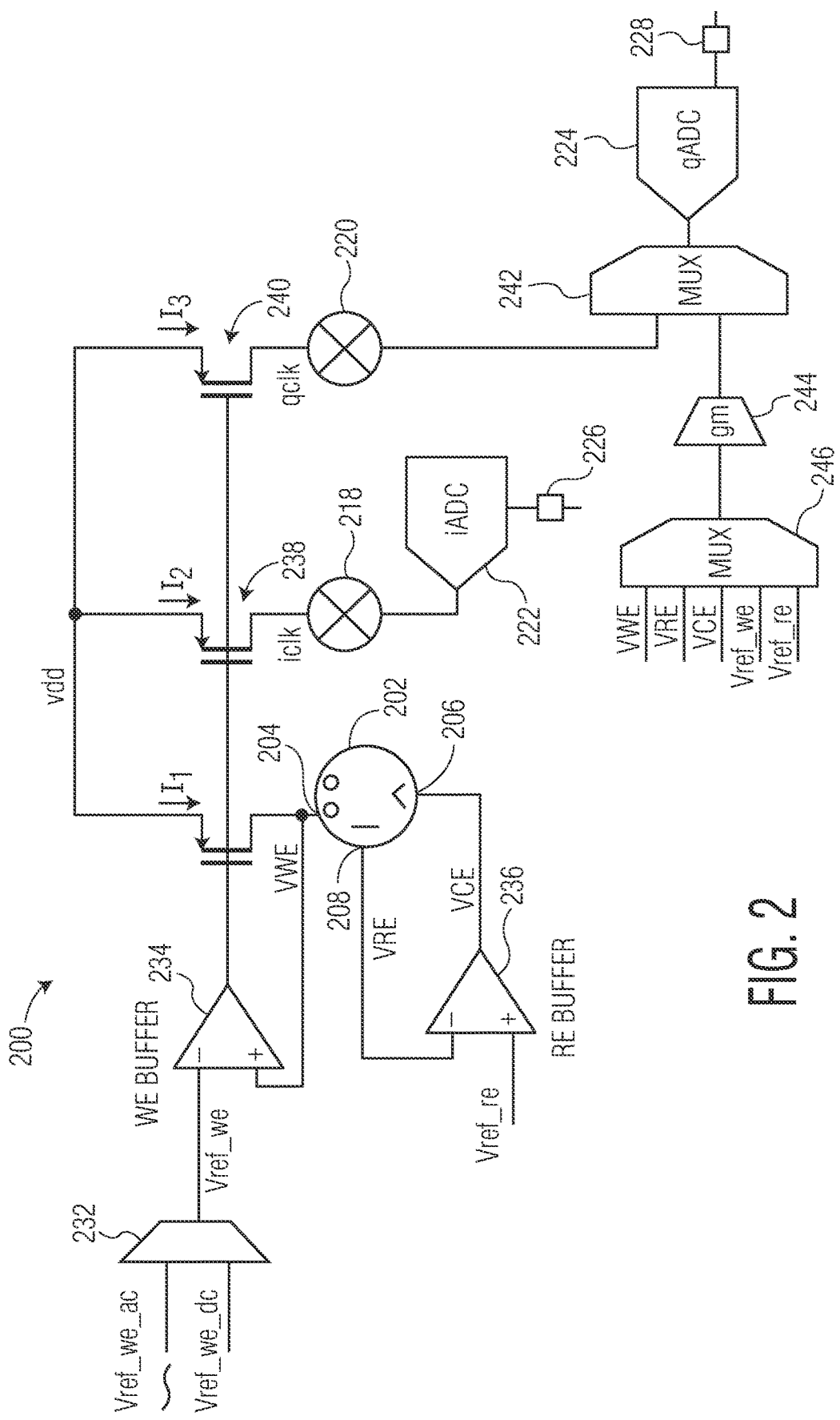
FIG. 2 is a block diagram of an analog front end coupled to an electrochemical sensor.

FIG. 2 is a block diagram of an analog front end (AFE) suitable for a health monitoring system 100 such as that of FIG. 1 or for use in a different system. The analog front end 200 is in the form of a potentiostat circuit. An electrode driver stage of the AFE applies a voltage across electrodes of an electrochemical sensor that is attached to a body or other test subject using an electrochemical sensor 202. The electrochemical sensor has a Work Electrode (WE) 204 that drives the voltage and a Counter Electrode (CE) that is the counterpart across the electrochemical sensor. The electrochemical sensor 202 detects the concentration of a chemical using an oxidation or reduction reaction. These reactions cause a flow of electrons across a membrane, substrate, or other material of the electrochemical sensor from the WE 204 to the CE 206 for an oxidation reaction or from the CE 206 to the WE 204 for a reduction reaction. The reaction typically occurs due to a voltage difference between an RE 208 of the sensor and the WE 204. The current flow is related to the concentration of the chemical that is being detected. The impedance and voltage across the terminals provide even more information about the test subject.

The electrode driver stage of the analog front end applies the voltage across the electrochemical sensor between the WE and a third electrode, the reference electrode (RE) 208. The AFE includes two amplifiers to maintain a constant voltage difference between the WE and the RE. One amplifier maintains the WE at a predetermined voltage. The other amplifier maintains the RE at the constant difference by controlling the voltage at the CE. The CE is a control node. The resulting current may be measured at either the WE or CE through measurement channels of the AFE. In the illustrated circuit, the WE current is measured. In order to maintain a constant potential, regardless of the current flowing between the WE and CE and to compensate for the voltage drop, a third electrode, a Reference Electrode (RE) 208 is used with many types of the electrochemical sensor. Accordingly, the WE 204 is configured for passing current and the RE 208 is configured to maintain the voltage. The AFE may be used with two terminal (WE, CE) electrochemical sensors or with three terminal (WE, CE, RE) electrochemical sensors.

The WE 204 is coupled to an alternating current (AC) voltage source, Vref_we_ac, and to a direct current (DC) voltage source, Vref_we_dc. These are generated by bias circuitry (not shown) and applied to a switch 232. The switch connects either the AC signal or the DC signal or both as a voltage to a WE buffer 234 of the electrode driver stage. The WE buffer 234 sets the voltage at the WE 204. The WE buffer 234 is in the form of a rail-to-rail class A operational transconductance amplifier (OTA) to provide a high impedance output. The switch 232 input is the negative input and the WE 204 is the positive input of the OTA.

An RE reference voltage, Vref_re also from the bias circuitry is applied to an RE buffer 236 of the electrode driver stage. The RE buffer keeps a constant reference voltage by driving the CE 206 of the electrochemical sensor 202. The RE buffer 236 is in the form of a rail-to-rail class AB OTA with a positive input coupled to the reference voltage, Vref_re, and the minus input coupled to the RE 208. The output is coupled to the CE 206. The WE 204 is coupled to a first current mirror 238 for an in-phase component and a second current mirror 240 for a quadrature phase component. The current mirrors each mirror out the electrochemical sensor current into a respective in-phase baseband analog-to-digital converter (ADC) 222 and a quadrature phase ADC 224. This may be referred to as indirect conversion.

A multiplexer 242 is provided to connect the second current mirror 240 with the quadrature phase ADC 224. The ADC outputs provide digital values for the measured parameter value. For an impedance measurement, the ADC outputs provide the measured impedance across the WE and RE terminals of the sensor. For a current measurement, the ADC outputs provide the measured direct current passing through the sensor. For a voltage measurement, the RE buffer 236 voltage that is applied to the RE 204 is applied through a gm stage 244 to the multiplexer 242 and is applied directly to the quadrature phase ADC 224 to provide at the output port 228 the measured DC voltage at the RE 204 of the sensor.

The indirect conversion of the sensor current mirrors the sensor current out of the WE buffer 234. This has the advantage that the sensor biasing of the current out of the WE buffer 234 is decoupled from the analog-to-digital conversion at the ADCs 222, 224. In other words, the sensor pins do not see any switching activity from the conversion components. This is good for the integrity of the sensor.

The WE buffer 234 provides the excitation voltage for the electrochemical sensor 202. The RE buffer 236 provides a DC voltage to act as a common virtual ground for each measurement. An alternating current (AC) voltage referred to herein may be generated by digital-to-analog converters (DAC) in the bias circuitry (not shown) or any other suitable reference voltage source. The voltage is injected into the sensor (not shown) through the three electrodes 204, 206, 208. The sensor presents an impedance to an applied voltage. The current, impedance, voltage, and other parameters through the sensor across the electrodes is measured by the electrochemical channel in the electrochemical sensor 202.

The analog front end 200 converts the received voltage or current from the electrochemical sensor to a digital value at output ports 226, 228. WE channels include a WE buffer 234, the current mirrors 238, 240 to amplify the signal from the electrodes, down mixers 218, 220 and the ADCs 222, 224. An in-phase down mixer 218 and a quadrature phase down mixer 220 mix the amplified alternating current voltage signal with the excitation frequency from the WE buffer 234 to down convert the electrode signal to a direct current (DC). This may also be referred to as mixing the measured AC current back to a DC current for the impedance measurement. The first mixer 218 receives an in-phase excitation signal to mix with the amplified signal to generate an in-phase (I) output. The second mixer 220 receives a quadrature phase excitation signal to generate a quadrature phase (Q) output. A selector or signal input switch (not shown) may be used to enable and disable the down converters in accordance with the sensing mode. The resulting current is coupled to the ADCs 222, 224 to generate respective I and Q numerical values to represent the sensed electrochemical body measurements, such as impedance between WE 204 and RE 208. In other sensing modes, the down mixers 218, 220 may be disabled.

In some embodiments, the ADCs are second order Continuous Time Sigma Delta (CTΣΔ) ADCs with a current input. The current (amperometric) and voltage measurements use one of the ADCs, while the EIS measurement uses both ADCs. An input multiplexer (MUX) (not shown, see FIG. 4) facilitates the voltage measurement.

At the inputs, both the RE buffer 236 and the WE buffer 234 have rail-to-rail input, the RE buffer 236 may be configured as a class AB amplifier. The relative voltages applied to WE 204 and RE 206 determine a DC voltage bias setpoint in terms of the difference, Vwe–Vre, in voltage between WE (Vwe) and RE (Vre). With changes to the relative voltage setpoints, the sensor 202 may be configured in different sink/source output current modes in order to enable different kinds of measurements, including different CGM (Continuous Glucose Monitoring) sensor redox reactions.

Different modes may be shown by changing some of the parameters of the circuit of FIG. 2. Consider a measurement result, $I_1$. $I_1$ is equal to the current generated by the sensor, that is the current that flows between WE 204 and RE 206 when the correct DC voltage bias setpoint, Vwe-Vre, is applied.

During a current measurement mode, such as an amperometric measurement mode, the Vref_we_dc DC setpoint is selected as the input of the WE buffer 234 by the switch 232. For this amperometric mode, the in-phase down mixer 218 (iclk) and the quadrature phase down mixer 220 (qclk) are not switching and the quadrature phase ADC 224 is off. Accordingly $I_2$, the current input to the in-phase ADC 222, is equal to $I_1$, the current through the WE 204. In this mode, the sensor current is converted to a digital form directly by the in-phase ADC 222 and provided at the one output port 226.

During an impedance measurement mode, such as an electrochemical impedance spectroscopy (EIS) measurement mode, the AC signal Vref_we_ac is selected by the switch 232 and applied to the WE buffer 234. The AC signal is superimposed on the DC signal, Vref_we_dc, creating a current $I_1$ at the WE 204 that may be characterized as in equation 1 as follows:

$$I_1 = I_{1dc} + I_{1ac} = I_{1dc} + \frac{V_{we} - V_{re}}{Z_{we\,re}} \quad \text{(Eq. 1)}$$

where $V_{we}$ is the voltage at WE 204, $V_{re}$ is the voltage at RE 208, and $Z_{we\,re}$ is the impedance between WE 204 and RE 208.

The input current $I_1$ from WE 204 is then mixed to DC with the same frequency of the AC excitation Vref_we_ac. In particular, the current $I_1$ is mixed into an in-phase component $I_2$, at the iclk down mixer 218 and the same current $I_1$ is mixed into a 90° phase shifted quadrature component $I_3$. The in-phase component $I_2$ is converted by the in-phase ADC 222 to generate an ADC output in a digital form at the output port 226, designated $iADC_{out}$. The quadrature component $I_3$ is converted by the quadrature phase ADC 224 to generate an output in a digital form at the output port 228 designated $qADC_{out}$.

In this way the real and the imaginary parts of the sensor impedance can be measured and calculated as shown in equations 2 and 3:

$$-\varphi_{sensor} = \tan^{-1}\left(\frac{qADC_{out}}{iADC_{out}}\right) \quad \text{(Eq. 2)}$$

where $\varphi_{sensor}$ is the phase of the WE 204 signal at a specified AC voltage excitation frequency $$|Z_{sensor}| = \frac{A_v}{\frac{\pi}{2}\sqrt{iADC_{out}^2 + qADC_{out}^2}} \quad \text{(Eq. 3)}$$

where $Z_{sensor}$ is the phase of the impedance of the WE 204 signal at the specified AC voltage excitation frequency, and $A_v$ is the amplitude of the AC signal excitation.

During a voltage measurement mode for the RE voltage, the DC voltage is read directly at the RE 208. One or more multiplexers 242 in the signal lines allow the functions of the ADCs to be changed. The signals applied to the sensor allow for voltage to be measured under specified conditions. A second multiplexer 246 allows several different DC voltages to be measured. In this configuration, the voltage of each electrode, VWE, VE, VCE is coupled to the second multiplexer 246 to allow the voltages to be coupled through the gm stage 244 and the first multiplexer 242 to be tested. In addition the reference voltages Vref_we and Vref_re are coupled to the second multiplexer and may also be measured at the second or quadrature phase ADC 224.

Figure 3:
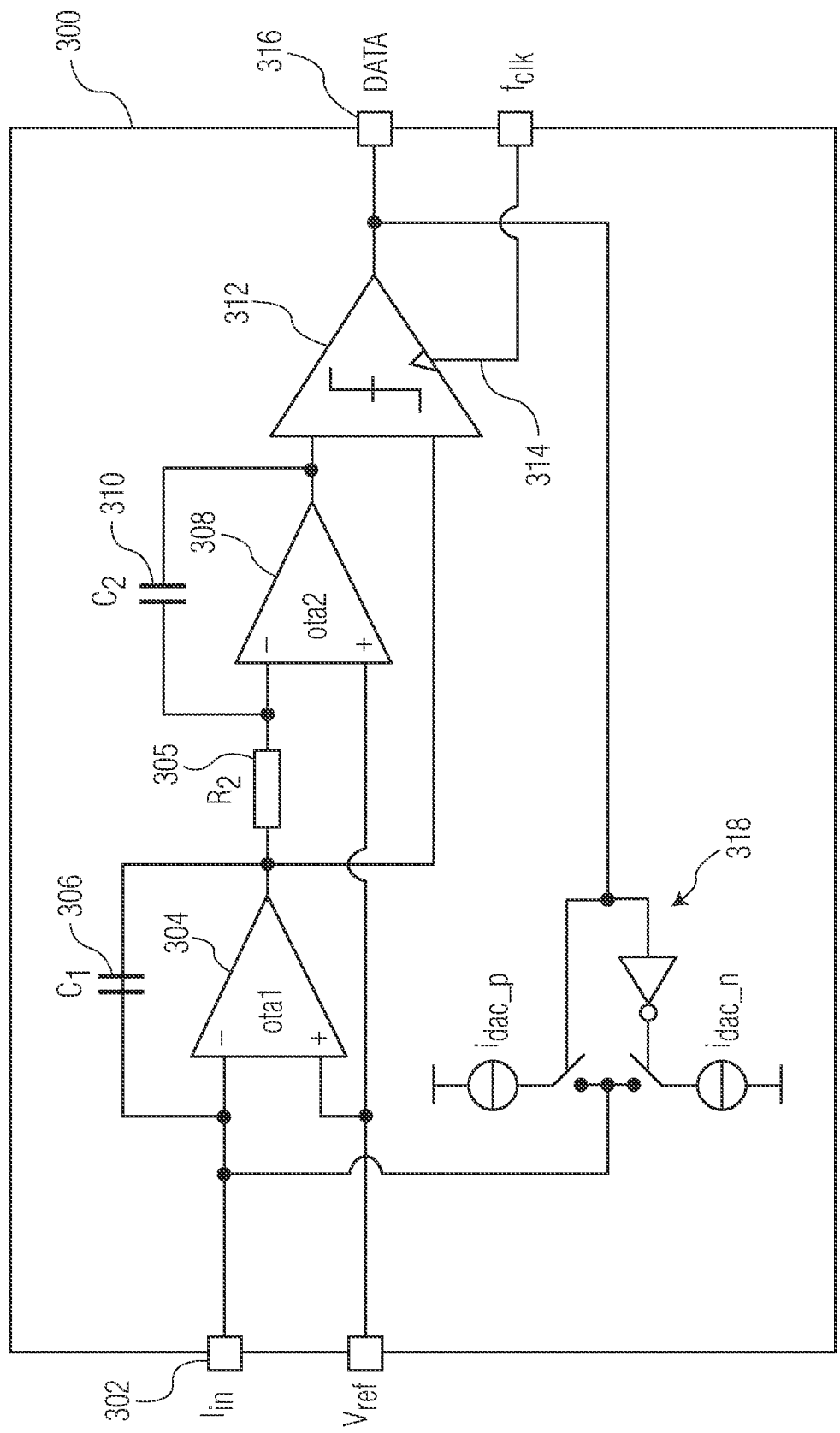
FIG. 3 is a simplified circuit diagram of a continuous time current input second order Sigma Delta analog-to-digital converter.

FIG. 3 is a simplified circuit diagram of a current input second order continuous time sigma delta (CTΣΔ) ADC suitable for use as the ADCs 222, 224 of FIG. 2 and with other described embodiments. A CTΣΔ ADC filters out-of-band signals to virtually eliminate them. It also eliminates any requirement for an anti-aliasing filter. The input signal, Iin, whether the in-phase component or the quadrature phase component is received at an input port 302 of the ADC 300. The input signal, Iin, is applied as an input to a first operational transconductance amplifier (OTA) 304 together with a reference voltage, Vref, input. The output is applied through a resistance 305 as an input to a second OTA 308 together with the same reference voltage, Vref.

A first capacitance 306 is coupled across the input to the first OTA 304 and the output of the first OTA 304 in the form of a capacitor. A second capacitance 310 is coupled across the input to the second OTA 308 and the output of the second OTA 308 in the form of a second capacitor. The capacitances 306, 310 absorb residual errors of the input current as it is received so that the ADC can operate using a current input. No resistor is needed at the input of the ADC to transform current into voltages.

The ADC 300 further includes a latched comparator 312 that operates on an input clock, fclk, 314 to generate a digital data result on an output port 316. A 1-bit DAC 318 is connected to the output port 316 and the input port 302 as a feedback loop. There may also be filters, interpolators, and a variety of other components to the ADC 300 (not shown). The described configuration is provided as an example and any of a variety of other ADCs may be used instead.

Figure 4:
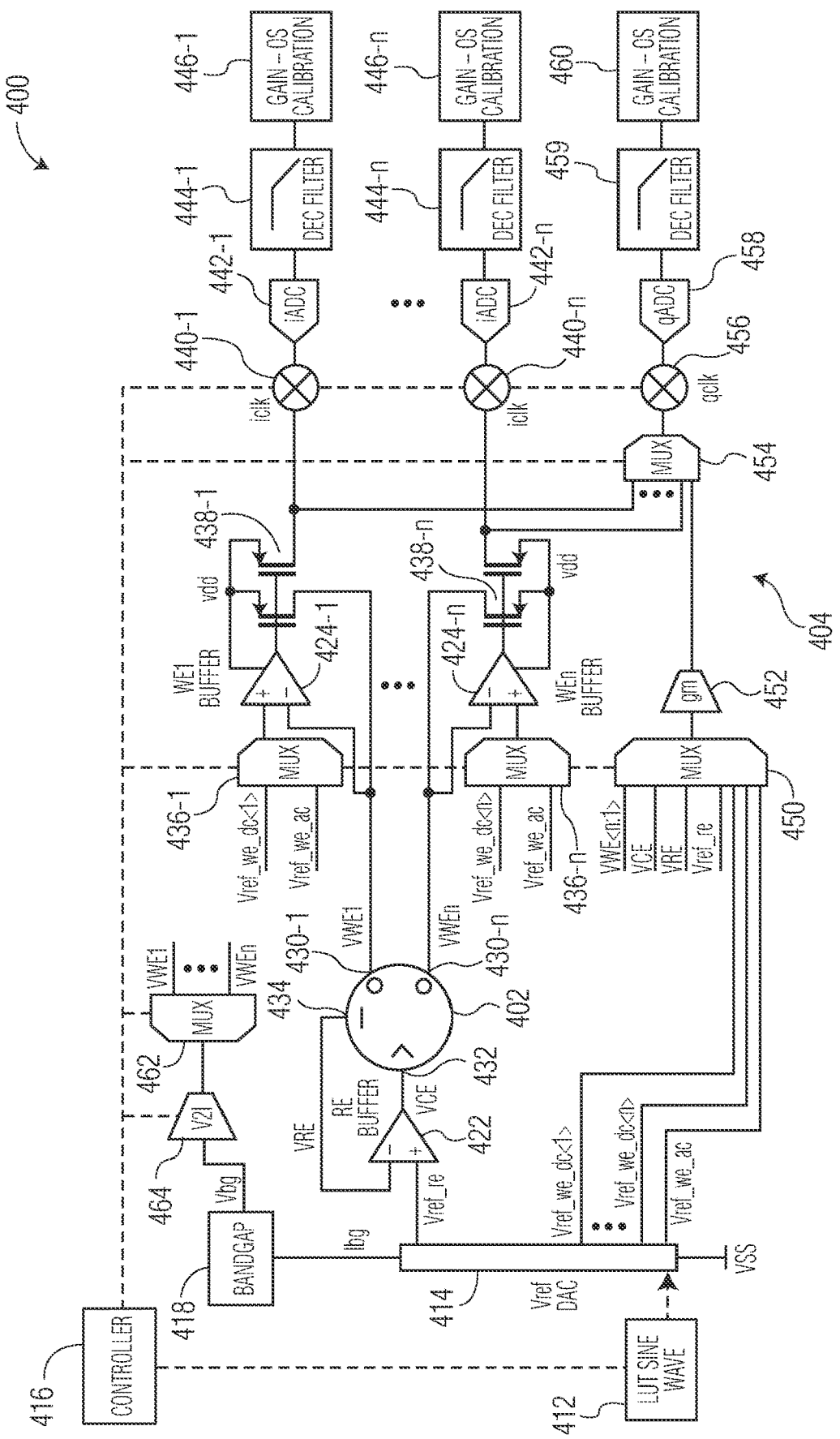
FIG. 4 is a diagram of an analog front end having a reconfigurable architecture coupled to an electrochemical sensor.

FIG. 4 is a simplified circuit diagram of a reconfigurable architecture for an analog front end (AFE) 400 for an electrochemical sensor 402 that has multiple measurement channels 404 so that it may be reconfigured for different measurement modes. The circuit may be seen as comprising building blocks from which different measurement configurations may be made. The operation of the AFE is in accordance with the principles described above with respect to FIGS. 2 and 3.

The AFE has bias circuitry to generate a bias to be applied to each of the electrodes of the electrochemical sensor. The bias circuitry includes a waveform library, for example a sine wave lookup table (LUT) 412 coupled to a digital-to-analog converter (DAC) 414 both controlled by a digital controller 416 and a bandgap core 418 also coupled to the DAC 414. The controller determines the appropriate sensing mode, for example current, impedance, and voltage and configures the rest of the bias circuitry, electrode driver stage, and measurement channels as appropriate for the sensing mode.

The sine wave LUT 412 provides a sequence of values to represent a sine wave with an appropriate amplitude and period. The set of values is read from an entry in a LUT of the sine wave LUT 412 which is selected from the controller. The DAC 414 receives the sequence of values and converts them to an analog wave form. As shown, the analog wave forms include Vref_re which drives a reference electrode buffer 422, Vref_we_ac which drives work electrode buffers from 1, 424-1, to n, 424-n, and Vref_we_dc<1> which drives the first work electrode buffer 424-1, to Vref_we_dc-n which drives the $n^{th}$ work electrode buffer 424-n. The various wave forms are adjusted by a bandgap current Ibg, from the bandgap core 418. The bandgap core generates a temperature compensated current Ibg over a trimmed resistance that is coupled to the DAC 414 to adjust the DC voltage output by the DAC 414.

The bias circuitry is coupled to an electrode driver stage. The electrode driver stage includes the RE buffer 422 and the n WE buffers 424-1 to 424-n which are coupled to the electrodes of the electrochemical sensor 402. The electrochemical sensor 402 has n work electrodes from 430-1 to 430-n, a counter electrode (CE) 432, and a reference electrode 434. In some embodiments, the RE buffer 422 and the WE buffers 424-1 to 424-n are OTAs or Op Amps with a negative input and a positive input and an output. The n WE buffers 424-1 to 424-n are each coupled at the negative input to a corresponding one of the work electrodes 430-1 to 430-n. The RE buffer 422 is coupled to the counter electrode 432 at its output and to the reference electrode 434 at its negative input. In some embodiments, the multiple work electrodes allow multiple simultaneous measurements to be taken using the one electrochemical sensor. In some embodiments, additional electrochemical sensors may be coupled to the AFE.

The positive inputs of the RE buffer and the WE buffers are coupled to the bias circuitry. The positive terminal of the RE buffer 422 is coupled to the Vref_re output of the DAC 414. The nature of the signal, Vref_re is determined by the controller 416 through the DAC 414 and adjusted by the bandgap current Ibg.

The positive terminal of each WE buffer 424-1 to 424-n is coupled to a particular AC or DC signal from the bias circuitry DAC 414 by the controller depending on the sensing mode. A first input multiplexer 436-1 is coupled to the positive input of the first WE buffer 424-1 at its output. The inputs to the first input multiplexer 436-1 are coupled to the Vref_we_dc<1> output of the DAC 414 and to the Vref_we_ac output of the DAC. The controller 416 selects either the DC signal Vref_we_dc<1> or the AC signal Vref_we_ac, or both, depending on the sensing mode. An input multiplexer before the WE buffer may be used in the same way for each of the n WE buffers. Accordingly, an $n^{th}$ input multiplexer 436-n is coupled to the positive input of the $n^{th}$ WE buffer 424-n at its output. The inputs to the $n^{th}$ input multiplexer 436-n are coupled to the Vref_we_dc-n output of the DAC 414 and to the Vref_we_ac output of the DAC. The controller 416 selects either the DC or the AC signal, depending on the sensing mode The AFE has multiple simultaneous sensor channels of the electrode driver stage which are activated and configured by the controller 416 to drive the electrodes 430-1 to 430-n, 432, 434 based on the sensing mode. The AFE also has multiple measurement channels which are activated and configured by the controller 416 to measure signals at the electrodes based on the sensing mode. A first measurement channel has a WE buffer 424-1, an ADC input stage 438-1, a down mixer 440-1, and an ADC 442-1. The ADC may optionally include or be followed by a decimation filter 444-1 and a gain and offset (os) calibration block 446-1. In the illustrated embodiment, each measurement channel has these components to the nth WE sensor channel with the nth WE buffer 424-n, an nth ADC input stage 438-n, a down mixer 440-n, and an ADC 442-n. There may optionally also be an nth decimation filter 444-n and a gain and offset calibration block 446-n. The decimation filter may be implemented as a digital filter to convert a bitstream from the ADC to a sequence of finite digital values at a selected resolution. The gain and offset calibration adjusts the sequence of finite digital values to compensate for errors and offsets in the system or measurements. The multiple measurement channels, each coupled to a work electrode allow multiple measurements to be made simultaneously or in sequence. The measurement results may be combined to obtain a more accurate measurement result. In some embodiments, measurement channels are coupled to the CE 432 or the RE 434 instead of or in addition to the WE 430-1 to 430-n.

A quadrature phase (q) input multiplexer 450 is a part of a Q sensor channel. There may be many Q sensor channels, but only one is shown for simplicity. Only one Q channel is used for the EIS and voltage measurements as described herein. The Q input multiplexer is coupled to the DAC 414 of the bias circuitry and receives WE buffer AC and DC signals and the reference voltage from the DAC, previously identified as Vref_we_dc<1> to Vref_we-dc-n, Vref_we_ac, and Vref_re. The Q input multiplexer 450 also receives the voltage output of the work electrodes, the counter electrode, and the reference electrode. The Q input multiplexer selects one of these signals as an output based on a command or signal from the controller 416. The output is coupled through a gm stage 452 to a down mixer input multiplexer 454. The gm stage may be implemented using a balanced operational transconductance amplifier with one or more stages or using any other suitable transconductance stage. It may be formed using differential amplifiers, cascodes, or other components and it conditions the output signal for use by the Q sensor channel.

The down mixer input multiplexer 454 couples its output to a Q down mixer 456 which is coupled to a qADC 458 and optionally to a Q decimation filter 459 and Q gain and offset calibration 460. The down mixer input multiplexer 454 has inputs coupled to each of the n ADC input stages 438-1 to 438-n. This allows any work electrode signal to be coupled to the Q down mixer to produce a quadrature phase output that is combinable with a corresponding in-phase down mixer output. The controller may select the appropriate ADC input stage signal for the selected sensing mode. The down mixer input multiplexer may also couple any of the signals from the Q input multiplexer 450 into the Q down mixer 456 for other sensing modes.

Considering the overall operation of the architecture of the AFE 400, the RE 434 and each WE 430-1 to 430-n are coupled to a feedback loop back into the RE buffer 422 and WE buffer 424-1 to 424-n, respectively. The feedback loop forces a selected DC voltage over the RE 434 and each WE 430-1 to 430-n. Both the RE buffer 422 and the WE buffers 424-1 to 424-n have been combined with a reconfigurable output stage that can sink or source current depending on the selected sensing mode, for example a reduction for oxygen or oxidation for peroxide. The combination with the reconfigurable output stage reduces the power consumption of the AFE overall and allows the output stage to connect to the respective ADC 442-1 to 442-n in the current domain through a simple mirroring, as indicated by the current mirrors 438-1 to 438-n.

For the ADCs 442-1 to 442-n a continuous time loop filter, current mode, second order, 1-bit Sigma Delta ADC as described in FIG. 3 may be used. Such an ADC is inherently linear. It can take advantage of oversampling at the DC inputs and the loop filter also acts as an anti-aliasing filter. While in some embodiments, the WE buffer and ADCs are shared. In other embodiments, there is a separate WE buffer and ADC for each work electrode. This avoids switching artifacts and allows sensing to be performed on all measurement channels simultaneously.

The AFE architecture also includes a calibration channel to determine the values used by the gain and offset calibration. Calibration may be performed in production or in the field when no electrochemical sensor is connected. The calibration channel receives a previously measured current that is injected into the calibration selector 462 from a voltage to current (V2I) converter 464 under control of the controller 416. The bandgap core 418 is a current and voltage generator that generates a reference voltage, Vbg, which is also coupled to the voltage to current converter 464 to provide the previously measured current. From the calibration selector 462, the current is also injected into measurement channels through corresponding WE buffers 424-1 . . . 424-n as selected through the connected multiplexers. The measurement channels include respective ADCs 442-1 . . . 442-n.

Figure 5:
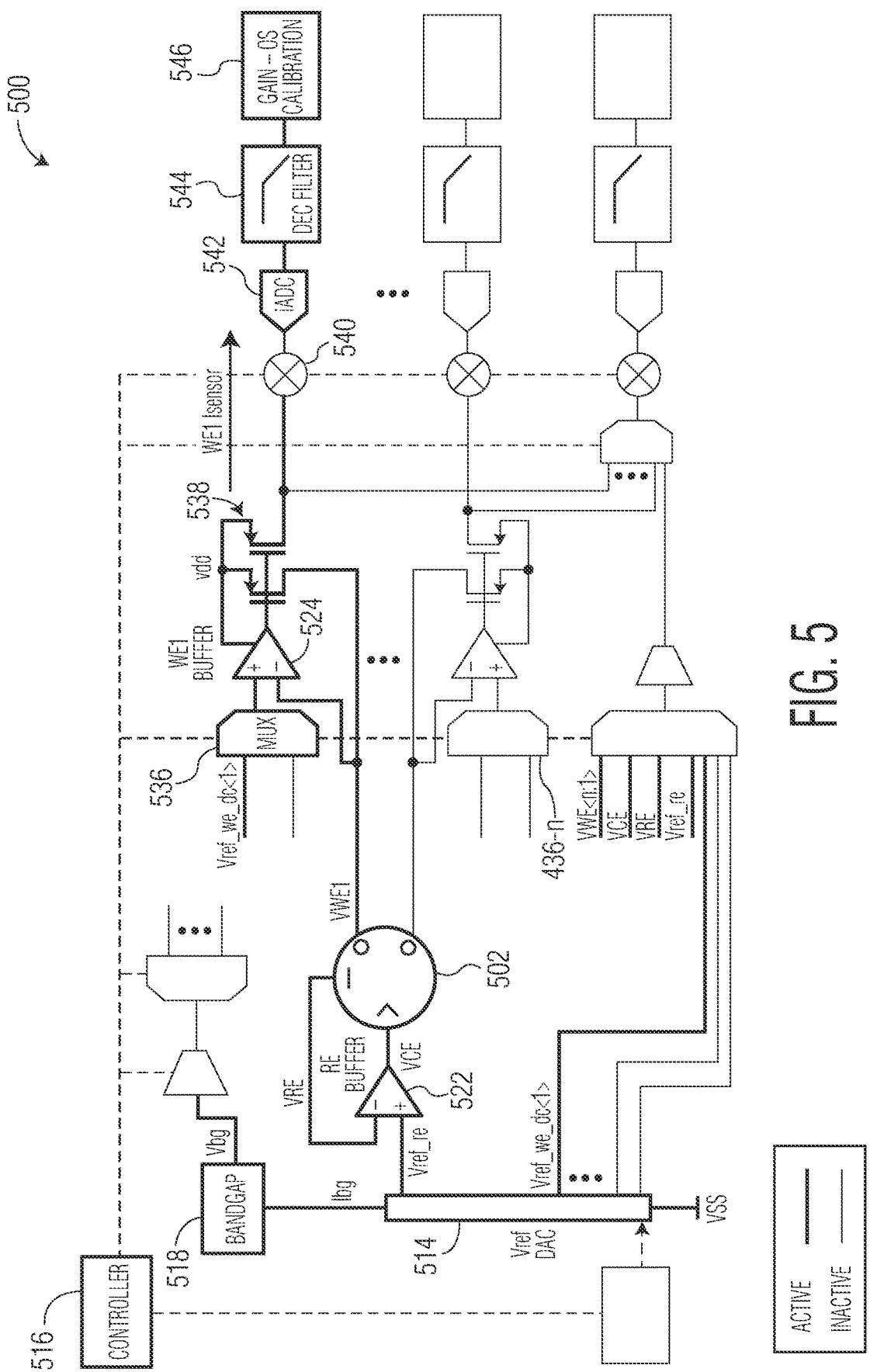
FIG. 5 is a diagram of the analog front end of FIG. 4 configured for a current measurement of a work electrode.

FIG. 5 is a diagram of an example configuration of a reconfigurable architecture of an AFE 500 for sensing a current identified as WE1 Isensor. A controller 516 configures the components for a current sensing mode. The elements are configured as active or inactive by the controller 516 for this current sensing configuration as indicated in FIG. 5. An electrode driver stage has a DAC 514 that generates work electrode DC signal, Vref_we_dc<1> to a WE buffer 524. This signal is coupled to the WE buffer 524 through an input multiplexer 536 that is configured by the controller 516 to supply that signal. The electrode driver stage further provides a reference voltage, Vref_re, for an RE buffer 522. The RE buffer 522 uses the voltage to drive the reference electrode and counter electrode as described above. There is no need for sine waves for these DC signals. The DC signals may also be generated with a different circuit instead of the DAC 514. The electrode driver stage also includes a bandgap core 518 to supply a bandgap current, Ibg, to the DAC 514, to adjust the DC signals. The electrode drive signal drives the electrodes of an electrochemical sensor 502 to generate a current at the work electrode.

The work electrode current is provided to a single measurement channel with a current mirror 538 coupled to an ADC 542 that is optionally coupled to a decimation filter 544 and calibration block 546. The output of the ADC is a measurement of the current from the work electrode sensor, WE1 Isensor.

For the current measurement configuration of FIG. 5, the controller 516 operates the DAC 514 to determine the two outputs the reference voltage, Vref_re and Vref_we_dc<1>. The controller 516 operates the input multiplexer 536 of the first measurement channel to select that the DC signal, Vref_we_dc<1>, provided by the DAC is applied to the WE buffer 524. The controller also disables a down mixer 540 between the WE buffer 524 and the first measurement channel ADC 542 so that the WE current passes directly from the work electrode of the electrochemical sensor 502 through the current mirror 538 to the first measurement channel ADC 542.

The controller also operates the other input multiplexers of the other measurement channels. In the configuration of FIG. 5, only one measurement channel is used for one work electrode current measurement. This is labeled as WE1 Isensor. There are multiple work electrodes (n work electrodes) and so the controller may alternatively, or in addition, configure the AFE to measure the current at one or more of the other work electrodes. Using the reconfigurable architecture of the AFE, the controller may operate the DAC 514 to supply additional DC signals to additional input multiplexers of additional WE buffers that are connected to additional measurement channels in the same manner as shown for the first measurement channel with the first ADC 542. As a result there may be additional current sensing modes with other or additional work electrodes. The particular configuration may be determined based on the nature of the electrochemical sensor and the chemicals that are to be sensed.

Figure 6:
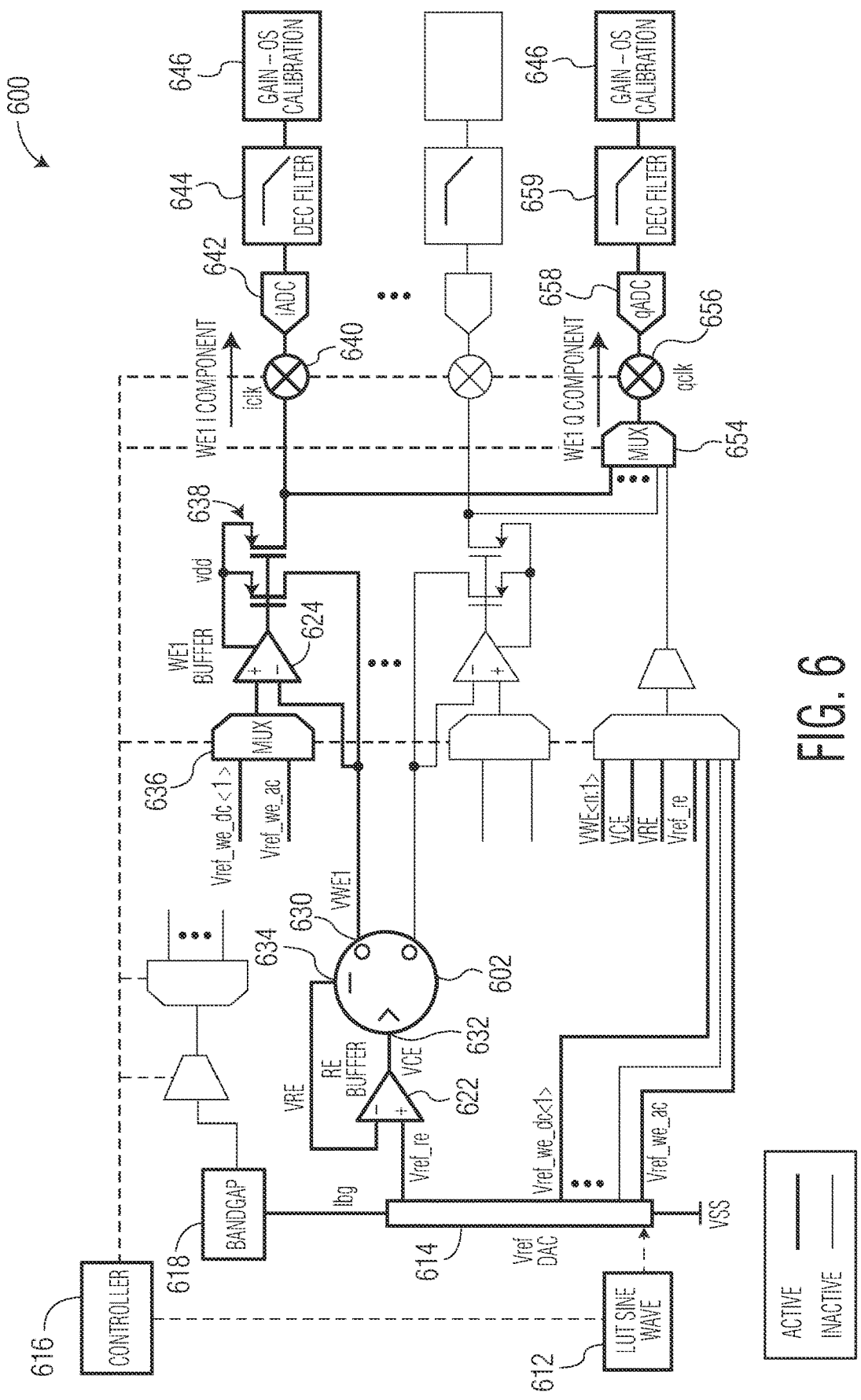
FIG. 6 is a diagram of the analog front end of FIG. 4 configured for an Electrochemical Impedance Spectroscopy measurement of a work electrode.

FIG. 6 is a diagram of an example configuration of a reconfigurable architecture for an AFE 600 for measuring an impedance using a measuring channel for an in-phase component and a measuring channel for a quadrature component. The elements are configured as active or inactive by the controller 616 for this impedance sensing configuration as indicated in FIG. 6. In this configuration, the electrode driver stage is configured by a controller 616 so that a DAC 614 or other reference signal generator is coupled to an RE buffer 622 to supply a reference voltage, Vref_re. The RE buffer 622 uses the reference voltage to drive an RE and a CE of an electrochemical sensor 602. The electrode driver stage also generates a WE DC signal, Vref_we_dc<1>, and a WE AC signal, Vref_we_ac, and is coupled to a WE buffer 624 through an input multiplexer 636 to a WE buffer 624. This signal from the electrode driver stage drives the WE of the electrochemical sensor 602. A bandgap core 618 or other circuit generates a bandgap current, Ibg, to regulate the DAC 614.

For the sensor impedance measurement (e.g., an EIS) in the impedance sensing mode, the bias block applies a temperature independent current, Ibg, to the DAC 614 to generate the DC signal, Vref_we_dc<1>, together with the AC signal, Vref_we_ac, of the DAC 614 which is built on top of the DC reference of the WE channel that is going to be measured. Since the RE buffer 622 is in a feedback loop, the sine wave AC signal, Vref_we_ac, is forced on top of the WE 630 of the electrochemical sensor 602. The RE buffer 622, and therefore the RE 634 or the electrochemical sensor 602, sees a DC voltage that serves as an AC ground. So the electrochemical sensor 602 sees a sine wave build between WE 630 and RE 634. This results in an AC current passing through the electrochemical sensor 602 that is mirrored by an active current mirror 638 coupled to the WE 630 and then measured. In the illustrated embodiment, the electrochemical sensor 602 has three terminals, WE 630, RE 634, and CE 632. The electrochemical sensor 602 has a finite impedance between WE 630 and RE 634 that is to be measured. In this example, this is done by applying an AC voltage as the AC signal output of the signal generator and reading an AC current.

The controller 616 commands a sine wave lookup table (LUT) 612 to deliver a selected set of sine wave coefficients from the lookup table to the DAC 614 that generates a sine wave output as the AC signal that goes to the WE buffer 624 and to the down mixers 640, 656 of the in phase and the quadrature phase (q) measurement channels. In this way, an AC voltage is built on top of the WE buffer 624 DC voltage without affecting the other reference voltages at the electrochemical sensor 602. When this AC voltage is forced on WE 630, an AC current that can change in polarity is detected at the WE 630 and measured. For this reason, the output stage of the WE buffer 624 is configured as class A.

The WE 630 output is supplied as an AC signal to an ADC input stage 638 including the current mirrors and from there to an in-phase down mixer 640 and a quadrature phase down mixer 656. The WE output current is mixed with the AC output, Vref_we_ac, of the DAC 614 in in-phase and quadrature phase to generate a current. At the first measurement channel, the WE measurement channel, the in-phase current, labeled as WE1 I component is coupled to an ADC 642, decimation filter 644 and calibration block 646 to provide the in-phase component. At the Q measurement channel the quadrature phase current, labeled as WE1 Q component is coupled to an ADC 658, decimation filter 659 and calibration block 646 to provide the in-phase component. These two components are used to develop a value for the impedance as described above.

The controller 616 has reconfigured the architecture of the AFE 600 to use two of the measurement channels, the first measurement channel and the Q measurement channel to generate I and Q components suitable for EIS measurements. The controller 616 operates the DAC 614 and the sine wave LUT 612 to generate both AC and DC work electrode signals, Vref_we_dc<1>, Vref_we_ac. The controller operates the input multiplexer 636 of the first measurement channel to select the AC signal, Vref_we_ac. The controller operates the down mixer 640 as an in-phase down mixer to down mix the work electrode signal from the current mirror of the ADC input stage 638 before it is applied to the ADC 642 of the first measurement channel. The controller also operates the Q measurement channel input multiplexer 654 to apply the work electrode signal from the ADC input stage 638 to the Q measurement channel down mixer 656 before it is applied to the Q measurement channel ADC 658.

Figure 7:
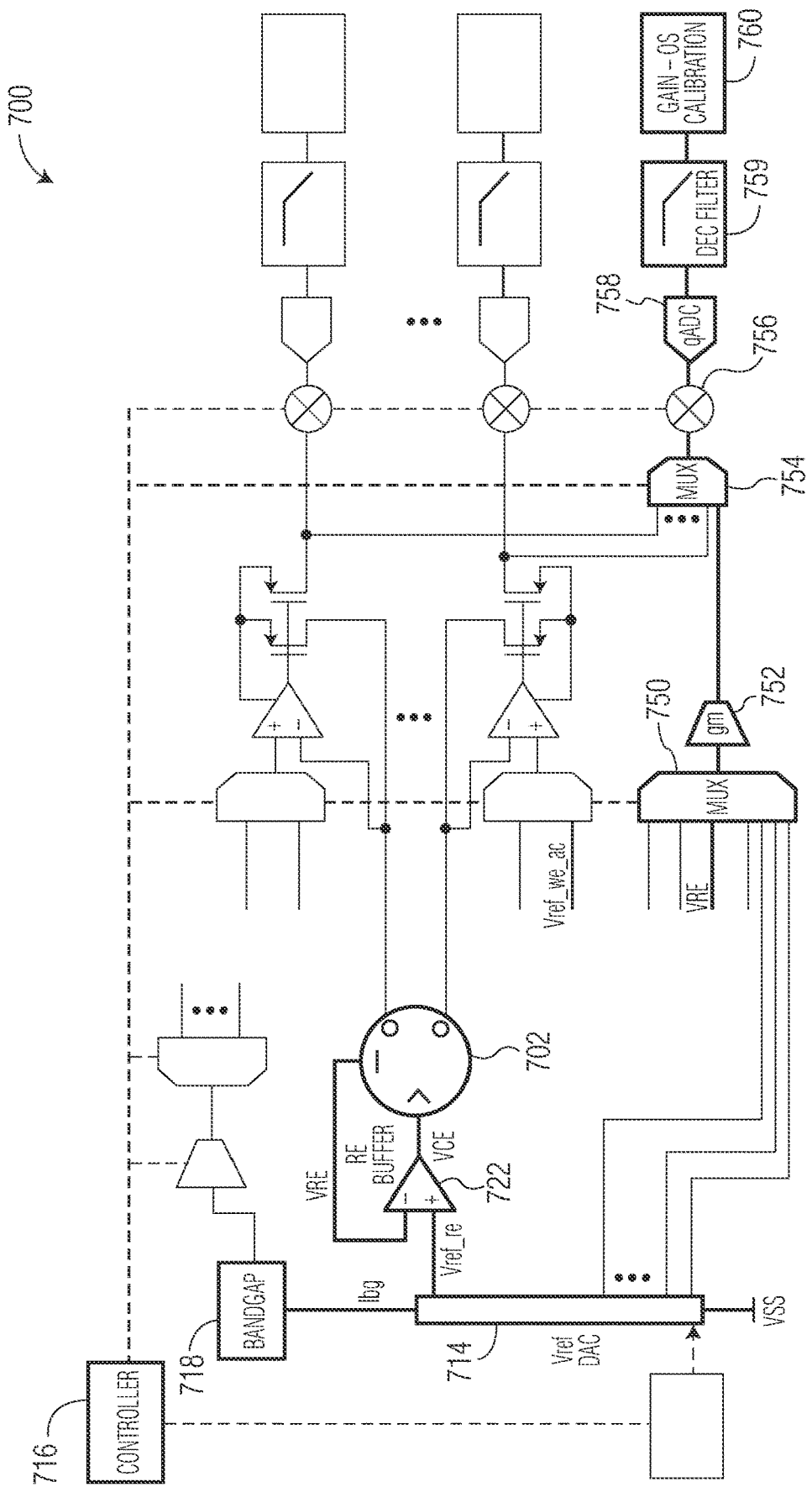
FIG. 7 is a diagram of the analog front end of FIG. 4 configured for a voltage measurement of a reference electrode.

FIG. 7 is a diagram of an example configuration of a reconfigurable architecture for an AFE 700 for sensing a voltage. The elements are configured as active or inactive by the controller 716 for this voltage sensing configuration as indicated in FIG. 7. In this configuration, the electrode driver stage generates a reference voltage, Vref_re, to an RE buffer 722 using a DAC 714 or any other reference voltage source, optionally adjusted by a bandgap core 718 under control of a controller 716. The RE buffer 722 in response to the reference voltage, Vref_re, generates VRE, a voltage that drives a reference electrode, RE, and VCE, a voltage that drives a counter electrode, CE, of an electrochemical sensor 702.

For sensing, a Q measurement channel is used, however, another measurement channel may be used instead. A Q input multiplexer 750 is configured to receive the voltage, Vre, from the reference electrode of the electrochemical sensor 702. This voltage is passed through a gm stage 752 to a down mixer input multiplexer 754 which couples the signal into an ADC 758, decimation filter 759 and calibration block 760 to generate a voltage value in a digital form corresponding to the reference electrode voltage, Vre. The controller 716 sets the outputs of the DAC 714 and the output selections of the Q input multiplexer 750 and the down mixer input multiplexer 754. The controller also disables the Q measurement channel down mixer 756 so that the reference electrode voltage, Vre, is passed directly to the ADC 758.

The controller 716 configures the reconfigurable architecture of the AFE 700 for the voltage measurement. The controller 716 operates the DAC 714 to provide only the reference voltage for the reference electrode, Vref_re. The controller operates the Q measurement channel input multiplexer 750 to supply the reference electrode signal to the Q measurement channel down mixer input multiplexer 754 and disables the down mixer before the Q measurement channel ADC 758. The controller disables the outputs of the other input multiplexers even those to the WE buffers and disables the down mixers of the other measurement channels. This allows for power savings in operation of this voltage measurement sensing mode. While the Q measurement channel is used, the AFE may be configured to use other measurement channels instead.

Figure 8:
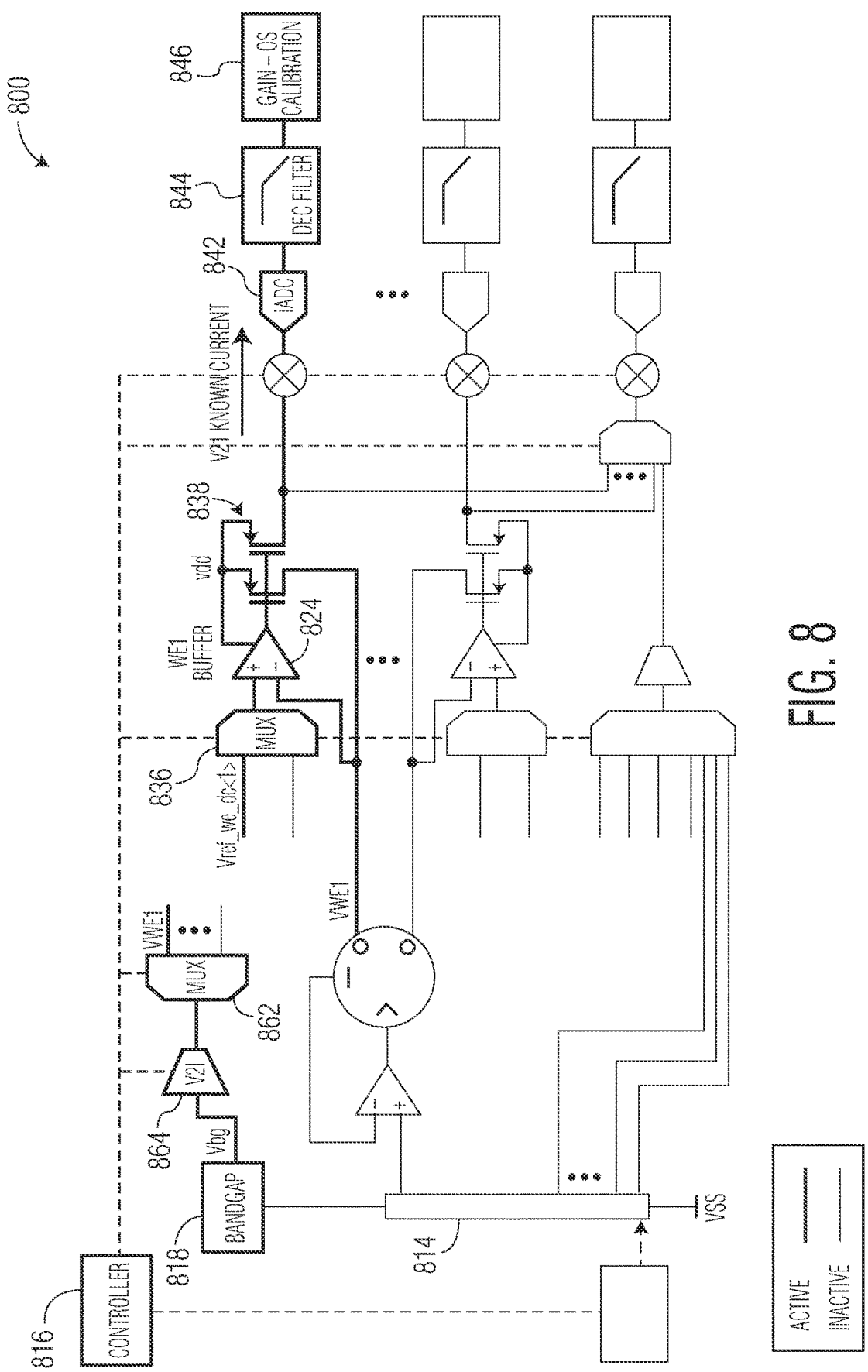
FIG. 8 is a diagram of the analog front end of FIG. 4 configured for a calibration.

FIG. 8 is a diagram of an example configuration 800 of the reconfigurable AFE architecture for calibration. The elements are configured as active or inactive by the controller 816 for this calibration configuration as indicated in FIG. 8. In embodiments, the calibration is for work electrode channel gain and offset calibration. A bandgap core 818 generates an accurate voltage, Vbg, that is coupled to a voltage to current (V2I) converter 864 under control of a controller 816.

An accurate voltage is then forced by a feedback loop over a trimmable resistance to generate the calibration current and the ADC reference current. In some embodiments, it may be assumed that the calibration currents need to be bidirectional, depending on the type of sensor used.

In the calibration sensing mode, the bandgap core 818 generates a bandgap voltage, Vbg, to a voltage to current converter (V2I) 864. The V2I 864 transforms the bandgap voltage, Vbg, into a current. The calibration sensing mode is operated when the system is not being used to measure data from the electrochemical sensor. To better isolate the measurement channel, the electrochemical sensor is not connected. In this mode, the current from the V2I 864 is coupled into a multiplexer 862 that connects the one current input into any of the multiple measurement channels that is being calibrated. To calibrate the measurement channel for the WE1 electrode 830, the current from the V2I 864 is connected to a WE1 pin and measured externally. For this measurement, a corresponding WE buffer 824 is disabled.

The measured current value is then injected into the WE buffer 824, the WE buffer 824 is turned on and the current is mirrored through a connected current mirror 838 and sent to an ADC 842. The result of the ADC is compared to the measured current. In some embodiments, a 0-input current is also measured by disabling the V2I 864. This allows for a two point gain and offset compensation which is applied to the gain and offset calibration 746 coupled to a decimation filter 844 at the ADC 842 output.

The multiplexer 862 is a one-to-many MUX that connects the V2I 864 to the measurement channel to be calibrated. The V2I provides a current output that serves as a substitute for the corresponding WE sensor 830 output that is coupled to the WE buffer 824. In other words, the V2I, as compared to an actual WE sensor in some modes generates only a current and not a voltage. The bias voltage is set by the WE buffer 824 or by an external component in some calibration approaches.

Figure 9:
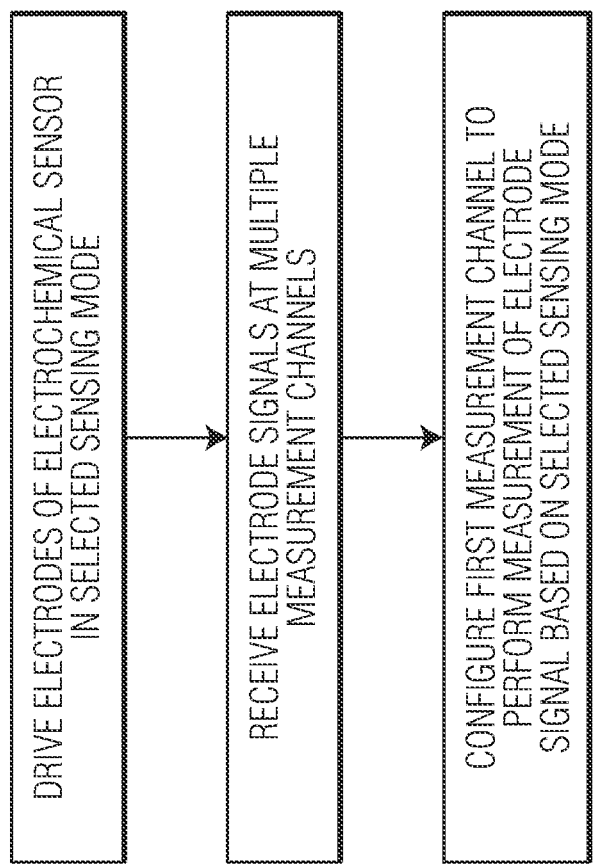
FIG. 9 is a process flow diagram of configuring an analog front end coupled to an electrochemical sensor for operation in different sensing modes.

FIG. 9 is a process flow diagram of operations performed by the analog front end described herein. At 902 driving electrodes of an electrochemical sensor in a selected one of multiple sensing modes is performed. At 904 receiving electrode signals from the electrodes of the electrochemical sensor at multiple measurement channels is performed. At 906 configuring a first measurement channel to perform a measurement of a received electrode signal based on the selected sensing mode is performed.

In some embodiments, driving the electrodes includes setting direct current voltage bias setpoints to drive the electrodes based on the selected one of the multiple sensing modes. As described above an electrode driver stage may be coupled to a controller that controls the direct current voltages and, in some sensing modes, alternating current voltages to the electrodes through current generators and buffers for the electrodes. In some embodiments, a first measurement channel includes an input multiplexer to select an input to the first measurement channel. One or all of the measurement channels may include input multiplexers. Configuring the measurement channel includes operating the input multiplexer based on the selected sensing mode.

Boundaries between the above-described operations are provided as examples. Multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

Alternatively, embodiments of the invention may be implemented entirely in hardware or in an implementation containing both hardware and software elements. In embodiments which use software, the software may include but is not limited to firmware, resident software, microcode, etc.

The connections as discussed herein may be any type of connection suitable to transfer signals or power from or to the respective nodes, units, or devices, including via intermediate devices. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, a plurality of connections may be replaced with a single connection that transfers multiple signals serially or in a time multiplexed manner. Likewise, single connections carrying multiple signals may be separated out into various different connections carrying subsets of these signals. The term "coupled" or similar language may include a direct physical connection or a connection through other intermediate components even when those intermediate components change the form of coupling from source to destination.

The described examples may be implemented on a single integrated circuit, for example in software in a digital signal processor (DSP) as part of a radio frequency integrated circuit (RFIC). The described examples may also be implemented in hardware in a field programmable gate array (FPGA) or application specific integrated circuit (ASIC), or in other electronic devices. The described examples may be implemented in analog circuitry, digital circuitry, or a combination of analog and digital circuitry. Alternatively, the circuit and/or component examples may be implemented as any number of separate integrated circuits or separate devices interconnected with each other in a suitable manner. These examples may alternatively be implemented as software or code representations of physical circuitry or of logical representations convertible into physical circuitry, such as in a hardware description language or any other appropriate form.

It will be readily understood that the components of the embodiments as generally described herein and illustrated in the appended figures may be arranged and designed in a wide variety of different configurations. Thus, the more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention may be practiced without one or more of the specific features or advantages of a particular embodiment. In other instances, additional features and advantages may be recognized in certain embodiments that may not be present in all embodiments of the invention.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An analog front end comprising:
   a controller;
   an electrode driver stage configured to be coupled to electrodes of an electrochemical sensor;
   wherein the electrodes include a Reference Electrode (RE), a Counter Electrode (CE), and a set of Work Electrodes (WEs);
   measurement channels coupled to the electrode driver stage to receive an electrode signal from the electrodes and to generate measurement results,
   wherein the measurement channels are configured to switch configurations to perform different measurements;
   wherein the electrode driver stage includes a set of WE buffers configured to drive the set of WEs, and an RE buffer to drive the RE; and
   wherein the controller sets a voltage at each of the WE buffers and a voltage at the RE buffer with a voltage difference to configure each of the measurement channels in different sink/source output current modes.

2. The analog front end of claim 1,
   wherein the measurement channels include an input multiplexer to select an input to the respective measurement channel,
   wherein the controller is configured to operate the input multiplexers based on a sensing mode of the analog front end.

3. The analog front end of claim 1,
   wherein the electrode driver stage comprises a digital to analog converter (DAC); and
   wherein the controller is configured to operate the DAC to generate signals based on a sensing mode of the analog front end.

4. The analog front end of claim 1,
   wherein a first measurement channel of the measurement channels is configured to switch configurations to perform a current measurement, a voltage measurement, and an impedance measurement.

5. The analog front end of claim 1:
   wherein the measurements include a current measurement, a voltage measurement, and an impedance measurement; and
   wherein each of the measurement channels are independently reconfigurable to simultaneously perform in parallel:
      only current measurements at a first time,
      only voltage measurements at a second time,
      only impedance measurements at a third time, and
      at least one current measurement in combination with at least one voltage measurement in combination with at least one impedance measurement at a fourth time.

6. The analog front end of claim 1:
   wherein a first one of the measurement channels is independently reconfigured to measure an in-phase component of an impedance; and
   wherein a second one of the measurement channels is independently reconfigured to measure a quadrature component of an impedance; and
   wherein the measurements are made simultaneously.

7. The analog front end of claim 1,
   wherein the RE is configured to keep a constant reference voltage by driving the CE and at least one of the WEs; and
   wherein a first measurement channel of the measurement channels comprises a potentiostat circuit.

8. The analog front end of claim 7,
   wherein the electrode driver stage is coupled to at least one of the WEs and the RE and configured to set a bias setpoint of the potentiostat circuit at a difference between a voltage at at least one of the WEs and a voltage at the RE.

9. The analog front end of claim 7,
wherein the electrode driver stage is configured to apply a direct current (DC) setpoint to at least one of the WE buffers to measure a current across the electrodes.

10. The analog front end of claim 7,
wherein the electrode driver stage is configured to set a bias setpoint of the potentiostat circuit at a difference between a voltage at at least one of the WEs and a voltage at the RE and
wherein a controller is configured to apply an alternating current (AC) signal to at least one of the WE buffers of the first measurement channel to measure an impedance across the electrodes.

11. The analog front end of claim 7,
wherein the electrode driver stage comprises an RE buffer to drive the CE, and
wherein the first measurement channel and a second measurement channel of the measurement channels are coupled to the RE buffer, and
wherein the RE buffer is configured as a common virtual ground to at least one of the WE buffers.

12. The analog front end of claim 1,
wherein each of the measurement channels include an ADC configured to generate a measurement result,
wherein at least one of the ADCs is a continuous time Sigma Delta ADC with a current input.

13. The analog front end of claim 12,
wherein an ADC of a first measurement channel of the measurement channels is coupled in a first configuration to convert a current measurement of the electrochemical sensor.

14. The analog front end of claim 12, further comprising a down mixer coupled to at least one of the WE buffers and to an alternating current applied at at least one of the WEs, and
an input multiplexer between the down mixer and the at least one of the WE buffers,
the input multiplexer being reconfigurable to down mix an output current from the at least one of the WEs with the alternating current to generate another current related to the output current from the at least one of the WEs,
the down mixer being coupled to the ADC to convert the another current to a digital form.

15. The analog front end of claim 12, further comprising a second continuous time Sigma Delta ADC with a current input coupled in a configuration to generate an Electrochemical Impedance Spectroscopy measurement.

16. The analog front end of claim 12,
wherein the RE buffer and the WE buffer have rail-to-rail inputs.

17. The analog front end of claim 1:
wherein each of the measurement channels are independently reconfigurable to simultaneously perform in parallel either a current measurement, a voltage measurement, or an impedance measurement.

18. The analog front end of claim 17:
wherein each of the measurement channels includes at least one of the WE buffers and an ADC for each of the WEs.

19. A health monitoring system comprising:
a controller;
a radio frequency system to send measurement results;
an electrochemical sensor having electrodes;
an electrode driver stage coupled to the electrodes of the electrochemical sensor; and
measurement channels coupled to the electrode driver stage to receive an electrode signal from the electrodes of the electrochemical sensor and to generate the measurement results,
wherein the controller is coupled to the measurement channels to switch configurations of the measurement channels to perform different measurements;
wherein the electrodes of the electrochemical sensor comprise a work electrode and reference electrode,
wherein the electrode driver stage comprises a work electrode buffer to drive the work electrode and a reference electrode buffer to drive the reference electrode, and
wherein the controller sets a voltage at the work electrode buffer and a voltage to the reference electrode buffer with a voltage difference to configure a first measurement channel of the measurement channels in different sink/source output current modes.

20. The health monitoring system of claim 19,
wherein the measurement channels include an input multiplexer to select an input to the respective measurement channel,
wherein the controller operates the input multiplexers based on a sensing mode of the analog front end, the sensing modes including a current measurement, a voltage measurement, and an impedance measurement.

21. An analog front end for an electrochemical sensor comprising:
an electrode driver stage coupled to electrodes of an electrochemical sensor; and
measurement channels coupled to the electrode driver stage to receive an electrode signal from the electrodes of the electrochemical sensor and to generate measurement results, the measurement channels configured to switch configurations to perform different measurements;
wherein the measurement channels comprise an ADC to generate a measurement result, the ADCs being in a form of a continuous time Sigma Delta ADC with a current input;
a down mixer coupled to a WE buffer and to an alternating current applied at the WE buffer, and
an input multiplexer between the down mixer and the WE buffer,
the input multiplexer being reconfigurable to down mix a WE output current with the alternating current to generate a current related to the WE output current,
the down mixer being coupled to the ADC to convert the current to a digital form.

* * * * *